United States Patent
Plumptre et al.

(10) Patent No.: US 10,518,038 B2
(45) Date of Patent: Dec. 31, 2019

(54) DRIVE MECHANISM AND INJECTION DEVICE HEREWITH

(71) Applicant: Sanofi, Paris (FR)

(72) Inventors: David Aubrey Plumptre, Worcestershire (GB); Simon Lewis Bilton, Warwickshire (GB)

(73) Assignee: Sanofi, Paris (FR)

( * ) Notice: Subject to any disclaimer, the term of this patent is extended or adjusted under 35 U.S.C. 154(b) by 591 days.

(21) Appl. No.: 14/915,417

(22) PCT Filed: Sep. 3, 2014

(86) PCT No.: PCT/EP2014/068654
§ 371 (c)(1),
(2) Date: Feb. 29, 2016

(87) PCT Pub. No.: WO2015/032781
PCT Pub. Date: Mar. 12, 2015

(65) Prior Publication Data
US 2016/0206828 A1 Jul. 21, 2016

(30) Foreign Application Priority Data
Sep. 3, 2013 (EP) .................................. 13182762

(51) Int. Cl.
*A61M 5/315* (2006.01)
*A61M 5/20* (2006.01)
(Continued)

(52) U.S. Cl.
CPC .......... *A61M 5/31553* (2013.01); *A61M 5/20* (2013.01); *A61M 5/31541* (2013.01);
(Continued)

(58) Field of Classification Search
CPC .......... A61M 5/31553; A61M 5/31541; A61M 5/31535; A61M 5/31583
See application file for complete search history.

(56) References Cited

U.S. PATENT DOCUMENTS

2006/0276754 A1* 12/2006 Kronestedt ............. A61M 5/20
604/186
2014/0107587 A1* 4/2014 Hogdahl ................. A61M 5/20
604/228

FOREIGN PATENT DOCUMENTS

EP      1974761       1/2008
WO      WO99/38554    1/1999
(Continued)

OTHER PUBLICATIONS

International Search Report and Written Opinion in International Application No. PCT/EP2014/068654, dated Feb. 6, 2015, 10 pages.
(Continued)

*Primary Examiner* — Nathan R Price
*Assistant Examiner* — Tasnim Mehjabin Ahmed
(74) *Attorney, Agent, or Firm* — Fish & Richardson P.C.

(57) ABSTRACT

A drive mechanism suitable for an injection device includes a housing, a piston rod at least axially movable relative to the housing, and a drive member which is coupled to the housing via a first clutch such that a relative rotation of the drive member about an axis of rotation with respect to the housing is prevented during dose setting and is allowed during dose dispensing. The drive member engages the piston rod such that a rotation of the drive member causes an axial movement of the piston rod. Re-engagement of the first clutch causes rotation of the drive member with respect to the housing in a direction moving the piston rod in the proximal direction.

15 Claims, 4 Drawing Sheets

(51) Int. Cl.
A61M 5/31 (2006.01)
A61M 5/32 (2006.01)

(52) U.S. Cl.
CPC ....... *A61M 5/31583* (2013.01); *A61M 5/3148* (2013.01); *A61M 5/3157* (2013.01); *A61M 5/31535* (2013.01); *A61M 5/31578* (2013.01); *A61M 5/3202* (2013.01); *A61M 2005/2026* (2013.01); *A61M 2005/2073* (2013.01); *A61M 2205/581* (2013.01); *A61M 2205/582* (2013.01)

(56) References Cited

FOREIGN PATENT DOCUMENTS

| | | |
|---|---|---|
| WO | WO2008/020023 | 2/2008 |
| WO | WO2009/146996 | 12/2009 |
| WO | WO2010/029043 | 3/2010 |
| WO | WO2011/026931 | 3/2011 |
| WO | WO2011/039203 | 4/2011 |
| WO | WO2012/128699 | 9/2012 |

OTHER PUBLICATIONS

International Preliminary Report on Patentability in International Application No. PCT/EP2014/068654, dated Mar. 8, 2016, 7 pages.

\* cited by examiner

DRIVE MECHANISM AND INJECTION DEVICE HEREWITH

CROSS-REFERENCE TO RELATED APPLICATIONS

This application is a U.S. national stage application under 35 USC § 371 of International Application No. PCT/EP2014/068654, filed on Sep. 3, 2014, which claims priority to European Patent Application No. 13182762.8, filed on Sep. 3, 2013, the entire contents of which are incorporated herein by reference.

TECHNICAL FIELD

The present invention relates to a drive mechanism which is suitable for an injection device, especially a pen type drug delivery device.

BACKGROUND

In the following, the distal end of an injection device or drive mechanism is referred to as the end where a cartridge and e.g. a needle are located, whereas the opposite end is the proximal end. A dose button may be provided at the proximal end.

The general function of a drive mechanism as defined above is to set a dose and to subsequently dispense the set dose. Dose setting (dose dialling) usually requires a user to manipulate one element of the drive mechanism, preferably to rotate a dial member e.g. via a dial grip. During dose dispensing the dial member may move, e.g. rotate, back to its original position wherein a drive member, which is not actuated during dose setting is moved together with the dial member during dose dispensing. The movement of the drive member may be a rotation, a displacement in the distal direction or a combined movement e.g. along a helical path. The drive member may act on a piston rod, e.g. a lead screw, for expelling medicament from a cartridge during dose dispensing.

In addition to this basic function of a drive mechanism it is in some cases preferred to allow a resetting of an already set dose, i.e. a correction or a deselecting of a dose. Preferably the user simply has to rotate the dial member, e.g. via a dial grip, in the opposite direction compared to the rotation during dose setting. Preferably, the drive member is not actuated during dose resetting, either.

At the beginning of dose setting, the mechanism is usually in a zero dose position, i.e. the previous dose has been fully administered and no new dose has been dialed. The user may set a dose up to a maximum dose which is defined by the mechanism, for example by providing an end stop which prevents setting of a higher dose. Typically, a maximum settable dose is 60, 80, 100 or 120 units of a medicament. During dose resetting, an already set dose may be reduced down to the zero dose position of the device. It is important that a user fully dispenses the required set dose to avoid an underdose which may have serious medical consequences. Thus, it is required to indicate to a user that the mechanism is in its zero dose position after dose dispensing.

To allow rotation of components of the drive mechanism, it is preferred if the components are mainly located concentrically about a common longitudinal axis of the drive mechanism. Thus, the components may have a tubular or sleeve-like shape. For example, the drive member and a dial or dose setting member may each be a tubular element. Some components may be provided surrounding other components fully or partly or may be provided one behind another.

An injection device comprising a housing, a piston rod which is in threaded engagement with a housing insert and a drive member is known from WO 99/38554 A1. During dose setting the drive member does not rotate relative to the housing. However, during dose dispensing a relative rotation of the drive member with respect to the housing is allowed. The drive member engages the piston rod such that a rotation of the drive member causes an axial movement of the piston rod. A ratchet is provided between the drive member and the housing insert allowing rotation of the drive member in only one direction.

A further injection device is known from EP 1 974 761 B1 wherein during dose setting, dose resetting and dose dispensing a dose grip and a dose dial sleeve rotate with respect to a housing and a housing insert between a zero dose position and a maximum dose position. A drive sleeve is provided with a clutch which is arranged such that a relative rotation of the drive member about an axis of rotation with respect to the housing is allowed during dose setting and is prevented during dose dispensing.

SUMMARY

Known injection devices typically comprise a cartridge containing a medicament. A bung or piston, which is usually made from a hyper-elastic or visco-elastic material, is located in the cartridge. One potential drawback of known injection devices is the effect of clearances within the mechanism as a result of designing for manufacturing tolerances or assembly which could lead to slight advancement of the piston rod and medicament dispense when the device is dialled for the subsequent dose. In other words a "weeping" might occur during dose setting which is undesired because of the loss of medicament and a potential confusion caused to a user of the device.

WO 2012/128699 A1 discloses a drug delivery device comprising a housing, a piston rod and a drive nut which are arranged such that rotation of the drive nut drives the piston rod forward. The drive nut is prevented from rotation by a ring shaped member of an actuation member. When the actuation member is pushed forward, the ring shaped member disengages with the drive nut and allows the drive nut to rotate. The device of WO 2012/128699 A1 further comprises a spring urging the piston rod and the drive nut in a retracting direction. This is intended to remove any play within the drive mechanism and to prevent drooling of medicament. The action of the spring does not cause rotation of the drive nut with respect to the housing in a direction moving the piston in the proximal direction. In addition, the action of the spring is independent of reengagement of the ring shaped member of the actuation member with the drive nut.

WO 2011/039203 A2 discloses a drug delivery device with a driver coupled to a piston rod. Relative rotation of the driver and the housing during dose setting is not prevented. Rather, a small rotational movement of the driver relative to the housing occurs during dose setting and after the dose setting operation. A ramp ring is provided as an additional component part interacting with the driver such that at the end of dose dispensing the driver carries out a small rotational movement which causes the piston rod to carry out an axial movement into the proximal direction.

Certain aspects of the present invention provide improved alternatives to the above solutions. Some aspects of the present invention, for example, relate to a drive mechanism and an injection device that prevent weeping during dose setting. The mechanism can include a housing, a piston rod which is at least axially movable relative to the housing and a drive member which is coupled to the housing via a first clutch such that a relative rotation of the drive member about an axis of rotation with respect to the housing is prevented during dose setting and is allowed during dose dispensing. Preferably, the drive member engages the piston rod such that a rotation of the drive member causes an axial movement of the piston rod. Further, this disclosure relates to an injection device including such a drive mechanism and a cartridge containing a medicament.

According to some aspects of the present invention, the first clutch is designed and arranged such that during engagement (or re-engagement) of the first clutch a rotation of the drive member with respect to the housing is generated in a direction moving the piston rod in the proximal direction. In other words, (re-)engagement of the first clutch causes retraction or back-winding of the piston rod, thus alleviating the force of the piston rod acting on the bung or piston in the cartridge. In some cases, this might create a small gap or clearance between the piston rod and the bung or piston in the cartridge. However, to prevent weeping during subsequent dose setting it is in most cases sufficient to re- duce the pressure within the cartridge by retraction or back-winding of the piston rod such that the piston rod is still in contact with the piston or bung. If engagement of the clutch between the housing and the drive member causes the axial movement of the piston rod, additional component parts, like a spring or a ramp ring may be omitted, thus making the device cheaper and less complex.

The piston rod is preferably in engagement with the housing and with the drive member, such that a rotation of the drive member with respect to the housing causes the axial movement of the piston rod. For example, the piston rod may be splined to the drive member and in threaded engagement with the housing. As an alternative, the piston rod may be splined to the housing and in threaded engagement with the drive member.

Preferably, (re-)engagement of the first clutch is effected by a relative axial movement of the drive member with respect to the housing and/or a housing insert (inner body). As an alternative, a clutch plate may be provided which is rotationally fixed to the housing and/or a housing insert. This clutch plate may be moved axially to disengage and to (re-)engage the first clutch.

According to a preferred embodiment, the first clutch comprises first teeth provided on the drive member and corresponding second teeth provided on the housing or a housing insert. Preferably, the first and/or second teeth are splines provided on a radially outer surface of a preferably tubular drive member and a radially inner surface of the housing or a housing insert, respectively. Generally, it would be sufficient if either the first teeth or the second teeth would comprise only one single tooth. However, to increase the torque bearable by the first clutch, it is preferred to provide several teeth on the drive member and on the housing or a housing insert, respectively. The teeth are uniformly disposed on the inner and outer circumference of the drive member and on the housing or a housing insert, respectively. Preferably, the number of teeth is chosen such that rotation of the drive member from one tooth to the adjacent tooth causes a movement of the piston rod corresponding to dispensing one unit of medicament from the cartridge.

There are several possibilities to cause a rotation of the drive member with respect to the housing during (re-) engagement of the first clutch. One alternative involves that the first teeth and/or the second teeth comprise a surface inclined to a plane which is parallel to the axis of rotation of the drive member by an angle of e.g. between 1° and 50°, preferably by an angle of 5° to 25°. Thus, the teeth may be angled and/or provided with ramps. As an alternative, the teeth may have a structure like a sliding block guide with a curved track.

Although it is desirable to reduce the total number of components of a drive mechanism, it might be useful for manufacturing reasons to split one or more components into separate elements. For example, the housing may comprise an outer body and an insert and/or an inner body which is axially and/or rotationally constrained to the outer body. In addition, a clutch may be designed by providing protrusions and/or recesses directly on the components which are to be coupled or decoupled by the clutch. As an alternative, a separate clutch element may be provided interposed between the two components which have to be coupled or decoupled.

In a preferred embodiment, the drive mechanism comprises an inner body rotationally constrained to the housing, wherein the second teeth are provided on the inner body. The inner body may be a component which is fixed to the housing such that the inner body and the housing behave like a single component. Alternatively, the inner body is a separate element which is rotationally constrained to the housing but axially displaceable.

To allow display of a set dose, the drive mechanism may comprise a number sleeve which is in threaded engagement with the housing or the inner body and which is movable between a zero dose position and a maximum dose position. Further, a zero dose stop may be provided on the number sleeve and/or the housing or the inner body which in the zero dose position prevents relative movement of the number sleeve with respect to the housing or the inner body in one rotational direction. The zero dose stop(s) preferably abut against each other at the end of dose dispensing thus limiting the rotation of the number sleeve.

The space between the teeth is usually small enough that the first clutch re-engages irrespective of the relative position of the teeth. However, it is preferred if the position of these teeth relative to the zero dose stop position of the number sleeve is such that the drive member rotates fractionally when the teeth engage, thus back-winding the piston rod away from the cartridge bung.

The drive mechanism according to some aspects of the present invention may be used in many different injection devices requiring different components. According to a first embodiment, the drive mechanism further comprises a dose setting member, a torsion spring arranged between the housing and the dose setting member, a second clutch rotationally decoupling the drive member and the dose setting member during dose setting and coupling the drive member to the dose setting member during dose dispensing and a button provided on the proximal end of the drive mechanism, wherein actuation of the button causes axial displacement of the drive member, de-coupling of the first clutch and coupling of the second clutch. According to a second embodiment, the drive mechanism further comprises a dose setting member, a torsion spring arranged between the housing and the dose setting member, a second clutch rotationally de-coupling the drive member and the dose setting member during dose setting and coupling the drive member to the dose setting member during dose dispensing and a trigger provided on a side of the housing, wherein actuation of the trigger causes axial displacement of a trigger clutch acting on the drive member, de-coupling of the first clutch and coupling of the second clutch.

According to a second embodiment, the drive mechanism further comprises a dose setting member, a torsion spring arranged between the housing and the dose setting member, a second clutch rotationally de-coupling the drive member and the dose setting member during dose setting and coupling the drive member to the dose setting member during dose dispensing and a trigger provided on a side of the housing, wherein actuation of the trigger causes axial displacement of a trigger clutch acting on the drive member, de-coupling of the first clutch and coupling of the second clutch.

According to a third embodiment, the drive mechanism further comprises a dose setting member, a compression spring arranged between the housing and the piston rod, a second clutch rotationally de-coupling the drive member and the dose setting member during dose setting and coupling the drive member to the dose setting member during dose dispensing and a button, wherein actuation of the button causes axial displacement of the dose setting member, de-coupling of the first clutch and coupling of the second clutch.

According to a fourth embodiment, the drive mechanism further comprises a dose setting member, a flat spring arranged between the housing and the drive member, a second clutch rotationally de-coupling the drive member and the dose setting member during dose setting and coupling the drive member to the dose setting member during dose dispensing and a button provided on the proximal end of the drive mechanism, wherein actuation of the button causes axial displacement of the drive member, de-coupling of the first clutch and coupling of the second clutch. The flat spring may either be provided wound directly on the housing and the drive member or preferably wound on spools attached to the housing and the drive member, respectively.

In certain aspects, an injection device may comprise a drive mechanism as mentioned above and a cartridge containing a medicament. Preferably, the compression spring of the third embodiment or the flat spring of the fourth embodiment is pre-tensioned to store the energy required to dispense the whole contents of the cartridge.

The term "medicament", as used herein, means a pharmaceutical formulation containing at least one pharmaceutically active compound, wherein in one embodiment the pharmaceutically active compound has a molecular weight up to 1500 Da and/or is a peptide, a proteine, a polysaccharide, a vaccine, a DNA, a RNA, an enzyme, an antibody or a fragment thereof, a hormone or an oligonucleotide, or a mixture of the above-mentioned pharmaceutically active compound, wherein in a further embodiment the pharmaceutically active compound is useful for the treatment and/or prophylaxis of diabetes mellitus or complications associated with diabetes mellitus such as diabetic retinopathy, thromboembolism disorders such as deep vein or pulmonary thromboembolism, acute coronary syndrome (ACS), angina, myocardial infarction, cancer, macular degeneration, inflammation, hay fever, atherosclerosis and/or rheumatoid arthritis, wherein in a further embodiment the pharmaceutically active compound comprises at least one peptide for the treatment and/or prophylaxis of diabetes mellitus or complications associated with diabetes mellitus such as diabetic retinopathy, wherein in a further embodiment the pharmaceutically active compound comprises at least one human insulin or a human insulin analogue or derivative, glucagon-like peptide (GLP-1) or an analogue or derivative thereof, or exendin-3 or exendin-4 or an analogue or derivative of exendin-3 or exendin-4.

Insulin analogues are for example Gly(A21), Arg(B31), Arg(B32) human insulin; Lys(B3), Glu(B29) human insulin; Lys(B28), Pro(B29) human insulin; Asp(B28) human insulin; human insulin, wherein proline in position B28 is replaced by Asp, Lys, Leu, Val or Ala and wherein in position B29 Lys may be replaced by Pro; Ala(B26) human insulin; Des(B28-B30) human insulin; Des(B27) human insulin and Des(B30) human insulin.

Insulin derivates are for example B29-N-myristoyl-des(B30) human insulin; B29-N-palmitoyl-des(B30) human insulin; B29-N-myristoyl human insulin; B29-N-palmitoyl human insulin; B28-N-myristoyl LysB28ProB29 human insulin; B28-N-palmitoyl-LysB28ProB29 human insulin; B30-N-myristoyl-ThrB29LysB30 human insulin; B30-N-palmitoyl-ThrB29LysB30 human insulin; B29-N-(N-palmitoyl-Y-glutamyl)-des(B30) human insulin; B29-N-(N-lithocholyl-Y-glutamyl)-des(B30) human insulin; B29-N-(ω-carboxyheptadecanoyl)-des(B30) human insulin and B29-N-(ω-carboxyhepta-decanoyl) human insulin.

Exendin-4 for example means Exendin-4(1-39), a peptide of the sequence H-His-Gly-Glu-Gly-Thr-Phe-Thr-Ser-Asp-Leu-Ser-Lys-Gln-Met-Glu-Glu-Glu-Ala-Val-Arg-Leu-Phe-Ile-Glu-Trp-Leu-Lys-Asn-Gly-Gly-Pro-Ser- Ser-Gly-Ala-Pro-Pro-Pro-Ser-NH2.

Exendin-4 derivatives are for example selected from the following list of compounds:

H-(Lys)4-des Pro36, des Pro37 Exendin-4(1-39)-NH2,
H-(Lys)5-des Pro36, des Pro37 Exendin-4(1-39)-NH2,
des Pro36 Exendin-4(1-39),
des Pro36 [Asp28] Exendin-4(1-39),
des Pro36 [IsoAsp28] Exendin-4(1-39),
des Pro36 [Met(O)14, Asp28] Exendin-4(1-39),
des Pro36 [Met(O)14, IsoAsp28] Exendin-4(1-39),
des Pro36 [Trp(O2)25, Asp28] Exendin-4(1-39),
des Pro36 [Trp(O2)25, IsoAsp28] Exendin-4(1-39),
des Pro36 [Met(O)14 Trp(O2)25, Asp28] Exendin-4(1-39),
des Pro36 [Met(O)14 Trp(O2)25, IsoAsp28] Exendin-4(1-39); or
des Pro36 [Asp28] Exendin-4(1-39),
des Pro36 [IsoAsp28] Exendin-4(1-39),
des Pro36 [Met(O)14, Asp28] Exendin-4(1-39),
des Pro36 [Met(O)14, IsoAsp28] Exendin-4(1-39),
des Pro36 [Trp(O2)25, Asp28] Exendin-4(1-39),
des Pro36 [Trp(O2)25, IsoAsp28] Exendin-4(1-39),
des Pro36 [Met(O)14 Trp(O2)25, Asp28] Exendin-4(1-39),
des Pro36 [Met(O)14 Trp(O2)25, IsoAsp28] Exendin-4 (1-39),
wherein the group -Lys6-NH2 may be bound to the C-terminus of the Exendin-4 derivative;
or an Exendin-4 derivative of the sequence
des Pro36 Exendin-4(1-39)-Lys6-NH2 (AVE0010),
H-(Lys)6-des Pro36 [Asp28] Exendin-4(1-39)-Lys6-NH2,
des Asp28 Pro36, Pro37, Pro38Exendin-4(1-39)-NH2,
H-(Lys)6-des Pro36, Pro38 [Asp28] Exendin-4(1-39)-NH2,
H-Asn-(Glu)5des Pro36, Pro37, Pro38 [Asp28] Exendin-4(1-39)-NH2,
des Pro36, Pro37, Pro38 [Asp28] Exendin-4(1-39)-(Lys)6-NH2,
H-(Lys)6-des Pro36, Pro37, Pro38 [Asp28] Exendin-4(1-39)-(Lys)6-NH2, H-Asn-(Glu)5-des Pro36, Pro37, Pro38 [Asp28] Exendin-4(1-39)-(Lys)6-NH2, H-(Lys)6-des Pro36 [Trp(O2)25, Asp28] Exendin-4(1-39)-Lys6-NH2, H-des Asp28 Pro36, Pro37, Pro38 [Trp(O2)25] Exendin-4(1-39)-NH2, H-(Lys)6-des Pro36, Pro37, Pro38 [Trp(O2)25, Asp28] Exendin-4(1-39)-NH2, H-Asn-(Glu)5-des Pro36, Pro37, Pro38 [Trp(O2)25, Asp28] Exendin-4(1-39)-NH2, des Pro36, Pro37, Pro38 [Trp(O2)25, Asp28] Exendin-4(1-39)-(Lys)6-NH2, H-(Lys)6-des Pro36, Pro37, Pro38 [Trp(O2)25, Asp28] Exendin-4(1-39)-(Lys)6-NH2, H-Asn-(Glu)5-des Pro36, Pro37, Pro38 [Trp(O2)25, Asp28] Exendin-4(1-39)-(Lys)6-NH2

H-(Lys)6-des Pro36 [Met(O)14, Asp28] Exendin-4(1-39)-Lys6-NH2, des Met(O)14 Asp28 Pro36, Pro37, Pro38 Exendin-4(1-39)-NH2, H-(Lys)6-desPro36, Pro37, Pro38 [Met(O)14, Asp28] Exendin-4(1-39)-NH2, H-Asn-(Glu)5-des Pro36, Pro37, Pro38 [Met(O)14, Asp28] Exendin-4(1-39)-NH2, des Pro36, Pro37, Pro38 [Met(O)14, Asp28] Exendin-4(1-39)-(Lys)6-NH2, H-(Lys)6-des Pro36, Pro37, Pro38 [Met(O)14, Asp28] Exendin-4(1-39)-(Lys)6-NH2, H-Asn-(Glu)5 des Pro36, Pro37, Pro38 [Met(O)14, Asp28] Exendin-4(1-39)-(Lys)6-NH2

H-Lys6-des Pro36 [Met(O)14, Trp(O2)25, Asp28] Exendin-4(1-39)-Lys6-NH2,

H-des Asp28 Pro36, Pro37, Pro38 [Met(O)14, Trp(O2)25] Exendin-4(1-39)-NH2,

H-(Lys)6-des Pro36, Pro37, Pro38 [Met(O)14, Asp28] Exendin-4(1-39)-NH2,

H-Asn-(Glu)5-des Pro36, Pro37, Pro38 [Met(O)14, Trp(O2)25, Asp28] Exendin-4(1-39)-NH2, des Pro36, Pro37, Pro38 [Met(O)14, Trp(O2)25, Asp28] Exendin-4(1-39)-(Lys)6-NH2, H-(Lys)6-des Pro36, Pro37, Pro38 [Met(O)14, Trp(O2)25, Asp28] Exendin-4(S1-39)-(Lys)6-NH2, H-Asn-(Glu)5-des Pro36, Pro37, Pro38 [Met(O)14, Trp(O2)25, Asp28] Exendin-4(1-39)-(Lys)6-NH2;

or a pharmaceutically acceptable salt or solvate of any one of the afore-mentioned Exendin-4 derivative.

Hormones are for example hypophysis hormones or hypothalamus hormones or regulatory active peptides and their antagonists as listed in Rote Liste, ed. 2008, Chapter 50, such as Gonadotropine (Follitropin, Lutropin, Choriongonadotropin, Menotropin), Somatropine (Somatropin), Desmopressin, Terlipressin, Gonadorelin, Triptorelin, Leuprorelin, Buserelin, Nafarelin, Goserelin.

A polysaccharide is for example a glucosaminoglycane, a hyaluronic acid, a heparin, a low molecular weight heparin or an ultra low molecular weight heparin or a derivative thereof, or a sulphated, e.g. a poly-sulphated form of the above-mentioned polysaccharides, and/or a pharmaceutically acceptable salt thereof. An example of a pharmaceutically acceptable salt of a poly-sulphated low molecular weight heparin is enoxaparin sodium.

Antibodies are globular plasma proteins (~150 kDa) that are also known as immunoglobulins which share a basic structure. As they have sugar chains added to amino acid residues, they are glycoproteins. The basic functional unit of each antibody is an immunoglobulin (Ig) monomer (containing only one Ig unit); secreted antibodies can also be dimeric with two Ig units as with IgA, tetrameric with four Ig units like teleost fish IgM, or pentameric with five Ig units, like mammalian IgM.

The Ig monomer is a "Y"-shaped molecule that consists of four polypeptide chains; two identical heavy chains and two identical light chains connected by disulfide bonds between cysteine residues. Each heavy chain is about 440 amino acids long; each light chain is about 220 amino acids long. Heavy and light chains each contain intrachain disulfide bonds which stabilize their folding. Each chain is composed of structural domains called Ig domains. These domains contain about 70-110 amino acids and are classified into different categories (for example, variable or V, and constant or C) according to their size and function. They have a characteristic immunoglobulin fold in which two β sheets create a "sandwich" shape, held together by interactions between conserved cysteines and other charged amino acids.

There are five types of mammalian Ig heavy chain denoted by α, δ, ε, γ, and μ. The type of heavy chain present defines the isotype of antibody; these chains are found in IgA, IgD, IgE, IgG, and IgM antibodies, respectively.

Distinct heavy chains differ in size and composition; α and γ contain approximately 450 amino acids and δ approximately 500 amino acids, while μ and ε have approximately 550 amino acids. Each heavy chain has two regions, the constant region (CH) and the variable region (VH). In one species, the constant region is essentially identical in all antibodies of the same isotype, but differs in antibodies of different isotypes. Heavy chains γ, α and δ have a constant region composed of three tandem Ig domains, and a hinge region for added flexibility; heavy chains μ and ε have a constant region composed of four immunoglobulin domains. The variable region of the heavy chain differs in antibodies produced by different B cells, but is the same for all antibodies produced by a single B cell or B cell clone. The variable region of each heavy chain is approximately 110 amino acids long and is composed of a single Ig domain.

In mammals, there are two types of immunoglobulin light chain denoted by λ and κ. A light chain has two successive domains: one constant domain (CL) and one variable domain (VL). The approximate length of a light chain is 211 to 217 amino acids. Each antibody contains two light chains that are always identical; only one type of light chain, κ or λ, is present per antibody in mammals.

Although the general structure of all antibodies is very similar, the unique property of a given antibody is determined by the variable (V) regions, as detailed above. More specifically, variable loops, three each the light (VL) and three on the heavy (VH) chain, are responsible for binding to the antigen, i.e. for its antigen specificity. These loops are referred to as the Complementarity Determining Regions (CDRs). Because CDRs from both VH and VL domains contribute to the antigen-binding site, it is the combination of the heavy and the light chains, and not either alone, that determines the final antigen specificity.

An "antibody fragment" contains at least one antigen binding fragment as defined above, and exhibits essentially the same function and specificity as the complete antibody of which the fragment is derived from. Limited proteolytic digestion with papain cleaves the Ig prototype into three fragments. Two identical amino terminal fragments, each containing one entire L chain and about half an H chain, are the antigen binding fragments (Fab). The third fragment, similar in size but containing the carboxyl terminal half of both heavy chains with their interchain disulfide bond, is the crystalizable fragment (Fc). The Fc contains carbohydrates, complement-binding, and FcR-binding sites. Limited pepsin digestion yields a single F(ab')2 fragment containing both Fab pieces and the hinge region, including the H—H interchain disulfide bond. F(ab')2 is divalent for antigen binding. The disulfide bond of F(ab')2 may be cleaved in order to obtain Fab'. Moreover, the variable regions of the heavy and light chains can be fused together to form a single chain variable fragment (scFv).

Pharmaceutically acceptable salts are for example acid addition salts and basic salts. Acid addition salts are e.g. HCl or HBr salts. Basic salts are e.g. salts having a cation selected from alkali or alkaline, e.g. Na+, or K+, or Ca2+, or an ammonium ion N+(R1)(R2)(R3)(R4), wherein R1 to R4 independently of each other mean: hydrogen, an optionally substituted C1-C6-alkyl group, an optionally substituted C2-C6-alkenyl group, an optionally substituted C6-C10-aryl group, or an optionally substituted C6-C10-heteroaryl group. Further examples of pharmaceutically acceptable salts are described in "Remington's Pharmaceutical Sciences" 17. ed. Alfonso R. Gennaro (Ed.), Mark Publishing Company, Easton, Pa., U.S.A., 1985 and in Encyclopedia of Pharmaceutical Technology.

Pharmaceutically acceptable solvates are for example hydrates.

BRIEF DESCRIPTION OF THE DRAWINGS

Certain aspects of the present invention will now be described in further detail with reference to the accompanying schematic drawings, wherein.

DETAILED DESCRIPTION

Figure 1:
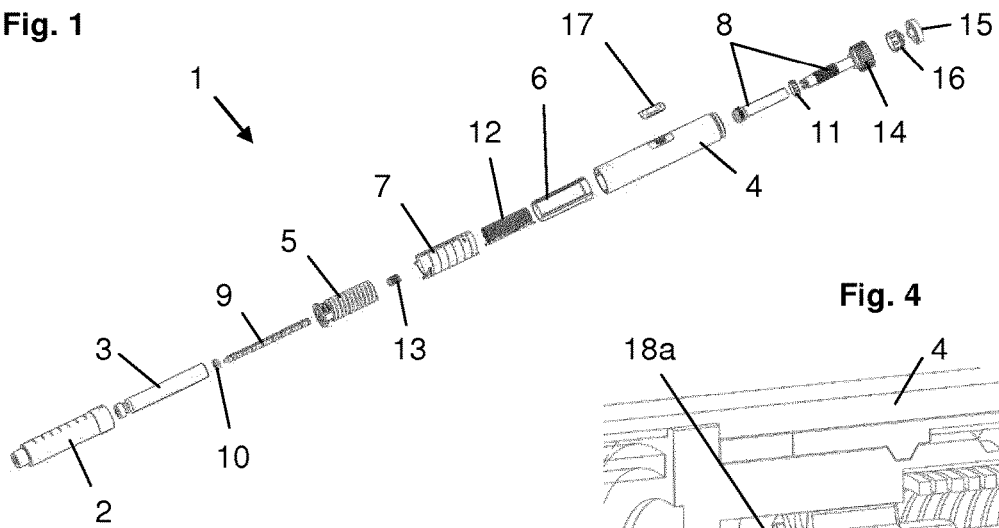
FIG. 1 shows an exploded view of an injection device comprising a drive mechanism according to a first embodiment of the invention.

An injection device 1 according to some aspects of the present invention is shown in FIG. 1 in an exploded view. The injection device 1 comprises a cartridge holder 2, a cartridge 3 and a drive mechanism. The drive mechanism comprises an outer housing 4, an inner housing 5, a dose dial sleeve as a dial member 6, a number sleeve as a display member 7, a drive sleeve as a drive member assay 8, a lead screw 9, a bearing 10, a nut 11, a drive spring 1 2, a return spring 13, a dial grip 14, a dose button 1 5 and a clutch plate 16. All components are located concentrically about a common principle axis of the mechanism. In more detail, the drive member assay 8 surrounds the lead screw 9, the torsion spring 12 surrounds the drive member 8, the dial member 6 and the inner housing 4 surround the torsion spring 1 2, the display member 7 surrounds the dial member 6 and the outer housing 4 surrounds the display member 7. Further, the nut 1 1 and the clutch plate 16 are located between the drive member assay 8 and the dial member 6. The drive member assay 8 is depicted comprising two components, which are rigidly fixed together. As an alternative, an integrally formed drive member 8 may be provided. Thus, in the following reference is made to drive member 8 meaning either an integrally formed or a two-part drive member.

Figure 2:
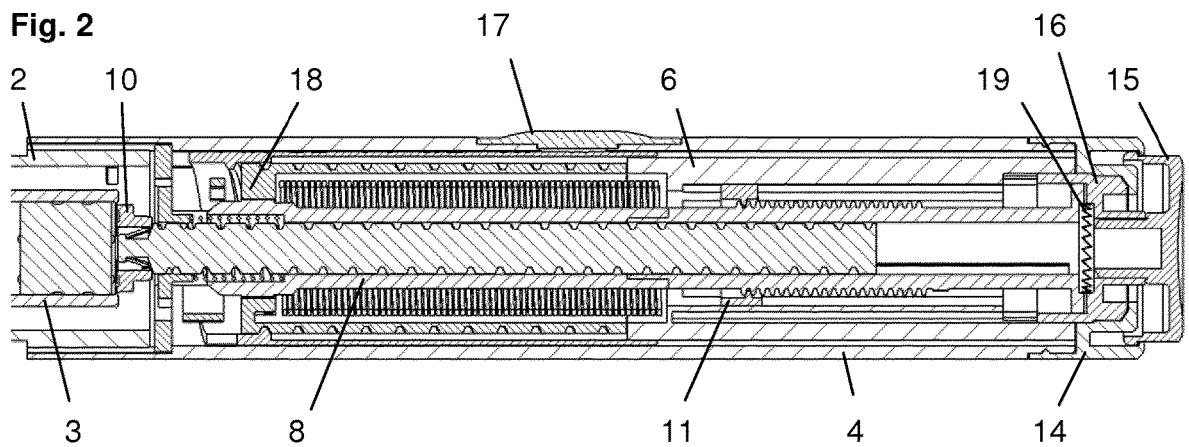
FIG. 2 shows a section view of the drive mechanism of FIG. 1 during dose setting.
Figure 3:
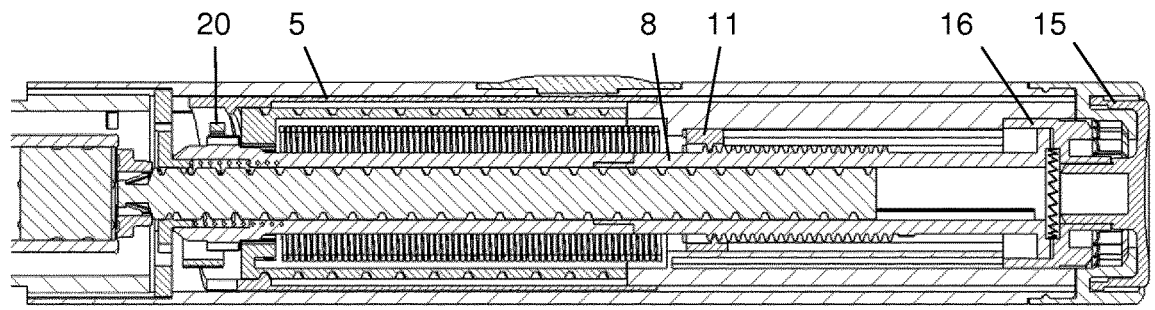
FIG. 3 shows an enlarged section view of the drive mechanism of FIG. 1 during dose dispensing.

A first clutch 18 is provided between the drive member 8 and the inner housing 5. A second clutch 19 is provided between the clutch plate 16 and the drive member 8. FIG. 2 shows the first clutch 18 in a position rotationally locking the drive member 8 to the inner housing 5, whereas the second clutch 19 allows relative rotation between the clutch plate 16 and the drive member 8. FIG. 3 shows the second clutch 19 in a position rotationally locking the clutch plate 16 to the drive member 8, whereas the first clutch 18 allows relative rotation between the drive member 8 and the inner housing 5. In FIG. 2 the drive member 8 is in a proximal position whereas in FIG. 3 the drive member 8 is displaced in a distal position. FIGS. 2 and 3 show the drive mechanism during dose setting and dose dispensing, respectively.

The dose button 15 is axially constrained to the clutch plate 16. As can be seen in FIG. 2, this may be achieved by a snap-on connection with the clutch plate 16 having an opening for receiving a pin of the dose button 15. Thus, the dose button 15 may be rotatable with respect to the clutch plate 16.

The dial grip 14 is axially constrained to the outer housing 4 which forms a body for the drive mechanism. Again, as shown in FIG. 3, this may be achieved by a snap-on connection between the dial grip 14 and the outer housing 4. The dial grip 14 is rotationally constrained to the clutch plate 16. In the embodiment of FIGS. 1 to 6 a splined interface is provided between the dial grip 14 and the clutch plate 16. This splined interface is disconnected when the dose button 15 is pressed, i.e. when the dose button 15 and the clutch plate 16 are moved axially relative to the dial grip 14 and the outer housing 4.

The clutch plate 16 is further rotationally constrained to the dial member 6. Again, a splined interface may be provided between the clutch plate 16 and the dial member 6. The clutch plate 16 is further coupled to the drive member 8 via a ratchet interface which occurs on axial abutment. The ratchet interface provides a detented position between the dial member 6 and the drive member 8 corresponding to each dose unit and engages different ramped tooth angles during clockwise and anti-clockwise relative rotation between the dial member 6 and the drive member 8. This ratchet interface forms the second clutch 19 with corresponding teeth provided on the clutch plate 16 and the drive member 8, respectively.

The display member 7 is rotationally constrained to the dial member 6. Again, a splined interface may be provided between the display member 7 and the dial member 6. The display member 7 is further constrained to move along a helical path relative to the inner housing 5. This may be achieved by a threaded interface between the display member 7 and the inner housing 5. As an alternative, a threaded interface may be provided between display member 7 and the outer housing 4. The display member 7 is limited to move between a zero dose position (distal position) and a maximum dose position (proximal position) which are defined by end stops, e.g. in the outer housing 4.

The display member 7 is marked with a sequence of numbers which are visible through a window 17 in the outer housing 4. As an alternative to a transparent window an aperture could be provided in the outer housing 4. The window 17 allows the user to denote the dialed dose of medicament. The window 17 may be or may comprise a magnifying lens. The window 17 may be an integral part of the outer housing 4 or a separate component attached to the housing.

The nut 11 acts as a last dose nut and is interposed between the dial member 6 and the drive member 8. The nut 11 is rotationally constrained to the dial member 6, e.g. via a splined interface. Thus, the nut 11 may be axially displaced relative to the dial member 6. The nut 11 moves along a helical path relative to the drive member 8, e.g. via a threaded interface, when relative rotation occurs between the dial member 6 and the drive member 8, i.e. during dose setting and dose resetting. An end stop (not shown) may be provided to limit the movement of the nut 11 in the track defined by the threaded interface. As an alternative to the depicted embodiment, the nut 11 may be splined to the drive member 8 and threaded to the dial member 6.

Figure 4:
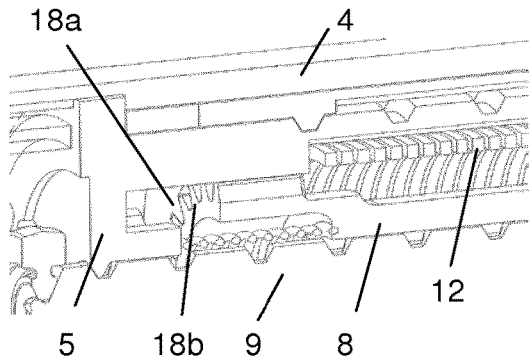
FIG. 4 shows a detail of the drive mechanism of FIG. 1 during dose setting.

The drive member 8 extends from the interface from the dial member 6 down to a splined tooth interface with the inner housing 5. This provides rotational constraint of the drive member 8 to the inner housing 5. The releasable splined tooth interface between the drive member 8 and the inner housing 5 forms the first clutch 18 with teeth 18a, 18b provided on the inner housing 5 and the drive member 8, respectively. Teeth 18a, 18b are depicted in FIG. 4 in more detail. Teeth 18a are provided on a radially inner surface of the inner housing 5 and teeth 18b are provided on a radially outer surface of the drive member 8. Teeth 18a, 18b are provided as splines each extending in the axial direction. As will be explained below in more detail, teeth 18a, 18b may be provided with an angled surface, i.e. inclined to a plane parallel the longitudinal axis, and/or with ramps (not shown in FIG. 4).

When the dose button 15 is pressed, the splined teeth of the first clutch 18 are disengaged and a ratchet feature 20 is engaged which provides an audible and/or tactile feedback during dose dispensing.

The inner housing 5 is rigidly fixed to the outer housing 4. Thus, neither any rotation nor any axial movement between the inner housing 5 and the outer housing 4 is possible. The inner housing 5 and the outer housing 4 may be formed as one integral part, however due to manufacturing reasons it is preferred to provide the housing as the two separate components of the outer housing 4 and the inner housing 5.

The drive spring 12 is a torsion spring which is attached at one end to the inner housing 5 and at the other end to the dial member 6. The drive spring 12 is pre-wound upon assembly, such that it applies a torque to the dial member 6 when the mechanism is at zero units dialled. The action of rotating the dial grip 14 to set a dose rotates the dial number 6 relative to the inner housing 5 and winds up the drive spring 12.

The lead screw 9 is rotationally constrained to the drive member 8 e.g. via a splined interface. When rotated, the lead screw 9 is forced to move axially relative to the drive member 8. This is achieved by a threaded interface between the lead screw 9 and the inner housing 5. The bearing 10 is axially constrained to the lead screw 9 and acts on the bung within the cartridge 3 during dose dispensing. This interface could be reversed so that the lead screw 9 is splined to the housing and threaded to the drive member 8. Further, as shown in the third embodiment, it is possible that the lead screw does not have a bearing.

The axial position of the drive member 8, the clutch plate 16 and the dose button 15 is defined by the action of the return spring 13 which abuts the inner housing 5 and applies a force on the drive member 8 in the proximal direction. This ensures that the clutch plate 16 is in splined engagement with the dial grip 14 and that the drive member 8 is in splined engagement with the inner housing 5. The return spring 13 also acts to maintain the engagement of the ratchet features between the drive member 8 and the clutch plate 16, i.e. to maintain the engagement of the second clutch 19. As an alternative, the function of the return spring 13 may be achieved fully or in part by the torsion spring 12.

The outer housing 4 provides location for the cartridge 3 and the cartridge holder 2 which can be attached to the outer housing 4. Further, the outer housing 4 comprises an interface to rigidly constrain the inner housing 5 and a groove on its external surface to axially retain the dial grip 14. Further, a removable cap may be provided which fits over the cartridge holder 2 and is retained via clip features. In an alternative embodiment the cartridge holder and body could be combined into a single component.

In the following, the functions and interactions of the above mentioned components will be described in more detail together with an explanation of the use of the drive mechanism of the injection device 1.

Regarding the first clutch 18 and the second clutch 19 there are two generally distinct states of the drive mechanism of the injection device 1 which are shown in FIGS. 2 and 3, respectively. FIG. 2 shows the drive mechanism in an at rest condition which is a condition if a user does not exert any forces on the drive mechanism. In this at rest condition the first clutch 18 couples the drive member 8 to the inner housing 5 and the second clutch 19 allows a relative rotation between the clutch plate 16 and the drive member 8. However, to rotate the clutch plate 16 with respect to the drive member 8, a torque has to be provided to overcome the resistance of the ratchet feature, i.e. the clutch plate 6 is not freely rotatable with respect to the drive member 8. The second condition which is shown in FIG. 3 occurs if a user depresses dose button 15. This decouples the first clutch 18 such that the drive member 8 is free to rotate with respect to the inner housing 5 and the second clutch 19 is coupled to prevent a relative rotation between the drive member 8 and the clutch plate 16.

With the device in the at rest condition, the display member 7 is positioned against its zero dose abutment with the inner housing 5 and the dose button 15 is not depressed. A dose marking "0" on the dial member 7 is visible through the window 17 on the outer housing 4. The drive spring 12 which has a number of pre-wound turns applied to it during assembly of the device applies a torque to the dial member 6. The dial member 6 is prevented from rotating under the action of the torque by its ratchet interface (second clutch 19) with the drive member 8. The drive member 8 is prevented from rotating by the interlock provided by the engagement of splined teeth on the drive member 8 and the inner housing 5 (first clutch 18). Return spring 13 maintains the first clutch 18 in its coupled state by pushing the drive member 8 in the proximal direction. However, the drive member 8 is free to be displaced in the distal direction against the force of the return spring 13 as the teeth of the second clutch 19 override each other upon a relative rotation between the drive member 8 and the clutch plate 16. The height of the teeth of the second clutch 19 is smaller than the axial height of the splines of the first clutch 18. Thus, the first clutch 18 remains in its coupled state even if the teeth of the second clutch 19 override each other.

The user selects a variable dose of medicament by rotating the dial grip 14 clockwise which generates an identical rotation in the dial member 6. Rotation of the dial member 6 causes wind up of the drive spring 12, increasing the energy stored within it. The drive member 8 is still prevented from rotating due to the engagement of its splined teeth with the inner housing 5 (first clutch 18 coupled). A relative rotation must therefore occur between the clutch plate 16 and the drive member 8 via the ratchet interface of the second clutch 19.

The user torque required to rotate the dial grip 14 is a sum of the torque required to wind up the drive spring 12 and the torque required to overhaul the ratchet feature of the second clutch 19. The return spring 12 is designed to provide an axial force to the ratchet feature and to bias the components (drive member 8, clutch plate 16, dose button 15) away from the cartridge end of the injection device 1. The axial load acts to maintain engagement of the ratchet teeth of the clutch plate 16 and the drive member 8. The torque required to overhaul the ratchet teeth is resultant from the axial load applied by the return spring 13, the clockwise ramp angle of the ratchet, the friction coefficient between the mating surfaces and the mean radius of the ratchet features.

As the user rotates the dial grip 14 sufficiently to increment the mechanism by one unit, the dial member 6 rotates relative to the drive member 8 by one set of ratchet teeth. At this point the ratchet teeth reengaged into the next detented position. An audible click is generated by the ratchet reengagement, and tactile feedback is given by the change in torque input required. Thus, the second clutch 19 forms a ratchet clicker.

Relative rotation of the dial member 6 and the drive member 8 causes a last dose nut 11 to travel along its threaded path towards its last dose abutment on the dial member 6. Rotation of the dial member 6 further generates rotation in the display member 7, which travels along its helical path defined by its interface with the inner housing 5. The dose marking corresponding to x units become aligned to the window 17 in the outer housing 4. The device is now set to deliver x units of liquid medicament.

With no user torque applied to the dial grip 14, the dial member 6 is now prevented from rotating under the action of the torque applied by the drive spring 12, solely by the ratchet engagement between the clutch plate 16 and the drive member 8 (second clutch 19). The torque necessary to overhaul the ratchet in the anti-clockwise direction is resultant from the axial load applied by the return spring 13, the anti-clockwise ramp angle of the ratchet, the friction coefficient between the mating surfaces and the mean radius of the ratchet features. The torque necessary to overhaul the ratchet must be greater than the torque applied to the dial member 6 (and hence clutch plate 16) by the drive spring 12. The ratchet ramp angle is therefore increased in the anti-clockwise direction to ensure this is the case.

The user may now choose to increase the selected dose by continuing to rotate the dial grip 14 in the clockwise direction. The process of overhauling the ratchet interfaces between the dial member 6 and the drive member 8 is repeated for each dose unit. Additional energy is stored within the drive spring 12 for each dose unit and audible and tactile feedback is provided for each unit dialed by the reengagement of the ratchet teeth. The torque required to rotate the dial grip 14 increases as the torque required to wind up the drive spring 12 increases. The torque requires to overhaul the ratchet in the anti-clockwise direction must therefore be greater than the torque applied to the dial member 6 by the drive spring 12 when the maximum dose has been reached.

If the user continues to increase the selected dose until the maximum dose limit is reached, the display member 7 engages with its maximum dose abutment on the outer housing 4, which prevents further rotation of the display member 7, dial member 6, clutch plate 16 and dial grip 14. At this point the maximum dose marking on the display member 7 is aligned to the window 17 in the outer housing 4.

Depending on how many units have already been delivered by a drive mechanism, during selection of a dose, the last dose nut 11 may contact its last dose abutment, i.e. the end stop with the dial member 6. The abutment prevents further relative rotation of the dial member 6 and the drive member 8 and therefore limits the dose that can be selected. The position of the last dose nut 11 is determined by the total number of relative rotations between the dial member 6 and the drive member 8, which have occurred each time the user sets a dose.

With the mechanism in a state in which a dose has been selected, the user is able to deselect or reset any number of units from this dose. Deselecting a dose is achieved by the user rotating the dial grip 14 anti-clockwise. The torque applied to the dial grip 14 by the user is sufficient, when combined with the torque applied by the drive spring 12 to overhaul the ratchet 19 between the clutch plate 16 and the drive member 8 in the anti-clockwise direction. When the ratchet is overhauled, anti-clockwise direction occurs in the dial member 6 (via the clutch plate 16) which returns the display member 7 towards the zero dose position, and unwinds the drive spring 12. The relative rotation between the dial member 6 and the drive member 8 causes the last dose nut 11 to return along its helical path, away from the last dose abutment.

With the mechanism in a state in which a dose has been selected, the user is able to activate the drive mechanism to commence delivery of a dose (dose dispensing). Delivery of a dose is initiated by the user depressing the dose button 15 on the top (proximal end) of the drive mechanism. When the dose button is depressed, it moves axially, acting on the clutch plate 16, which in turn acts on the drive member 8. The clutch plate 16 disengages its spline teeth from the dial grip 14 and after that the drive member 8 disengages its spline teeth (first clutch 18) from the inner housing 5.

When the splined interface of the first clutch 18 between the inner housing 5 and the dive member 8 disengages, the interface which prevents rotation of the drive member 8 during selection of a dose is removed. The torque applied to the dial member 6 from the drive spring 12 is transmitted, via the ratchet interface of the second clutch 19 into the drive member 8. This torque causes the drive member 8 and hence, due to its relative engagement with the inner housing 5, advancement of the lead screw 9. Axial displacement of the lead screw 9 forces liquid medicament to be delivered from the mechanism, by the action of the bearing 10 which contacts and displaces the bung within the cartridge 3.

The ratchet feature 20 of the inner housing 5 comprises a clicker arm (not shown). The clicker arm is a compliant cantilever beam integrated into the inner housing 5, which interfaces radially with the spline ratchet teeth 18b in the drive member 8. The ratchet teeth 18b spacing corresponds to the drive member 8 rotation required to deliver a single dose unit. During dispense, as the drive member 8 rotates, the spline features engage with the clicker arm to produce an audible click with each dose unit delivered. The torque required to overhaul the clicker arm is resultant from the ratchet teeth profile, the stiffness of the cantilever beam and the nominal interference between the clicker arm and the ratchet. The clicker arm interface is designed such that the torque required to overhaul is significantly less than the torque provided by the drive spring 12.

The rotation of the dial member 6 also causes the display member 7 to return along its helical path, relative to the inner housing 5, towards the zero dose abutment. Delivery of a dose continues via the mechanical interactions described above while the user continues to depress the dose button 15. If the user releases the dose button 15, the return spring 13 returns the dose button 15 to its at rest position via the drive member 8 and the clutch plate 16 such that the drive member 8 becomes rotationally constrained and delivery of a dose is halted.

With the dose button 15 depressed, delivery of a dose continues until the display member 7 reaches its zero dose abutment with the inner housing 5. The torque applied to the dial member 6 is reacted by the abutment of the display member 7 and the dial member 6, wherein the clutch plate 16 and the drive member 8 are prevented from rotating further. During delivery of a dose, the drive member 8 and the dial member 6 rotate together, so that no relative motion in the last dose nut 11 occurs. The last dose nut 11 therefore travels towards its abutment on the dial member 6 during dose setting only and travels away from the end stop during dose resetting.

Once the delivery of a dose is stopped by the display member 7 returning to the zero dose abutment, the user may release the dose button 15 which will reengage the first clutch 18 between the inner housing 5 and the drive member 8. The mechanism is now returned to the at rest condition.

According to the present invention, the spline teeth 18a, 18b on either the drive member 8 or inner housing 5 are angled so that when the dose button 15 is released the reengagement of the spline teeth fractionally backwind the drive member 8 thereby removing the engagement of the display member 7 to the zero dose stop abutment in the inner housing 5. This removes the effect of clearances in the drive mechanism (for example due to tolerances) which could otherwise lead to slight advancement of the lead screw 9 and medicament dispense when the drive mechanism is dialled for the subsequent dose. This is due to the zero dose stop of the display member 7 no longer restraining the mechanism and instead the restraint returning to the splines 18a, 18b between the drive member 8 and the inner housing 5. FIG. 4 shows the first clutch 18 in its reengaged state.

Figure 5:
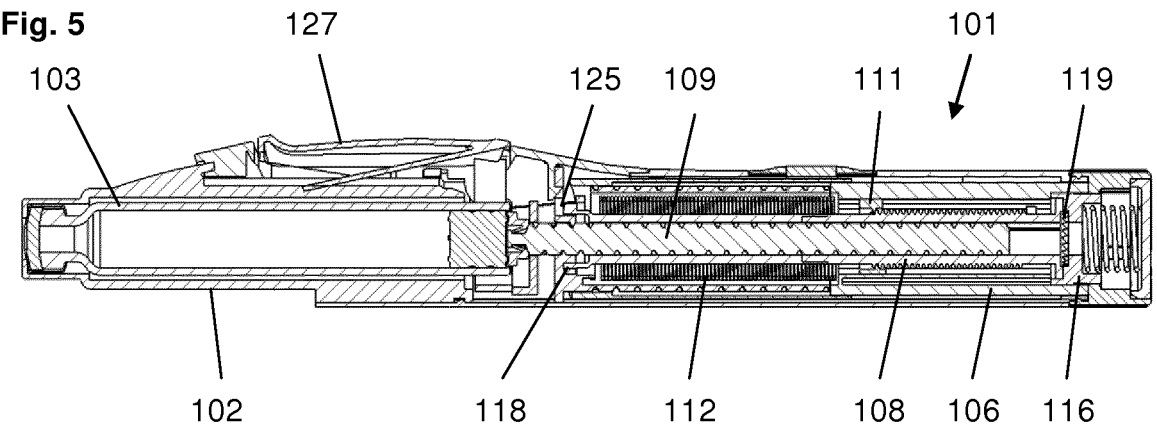
FIG. 5 shows a section view of an injection device comprising a drive mechanism according to a second embodiment of the invention during dose setting.
Figure 6:
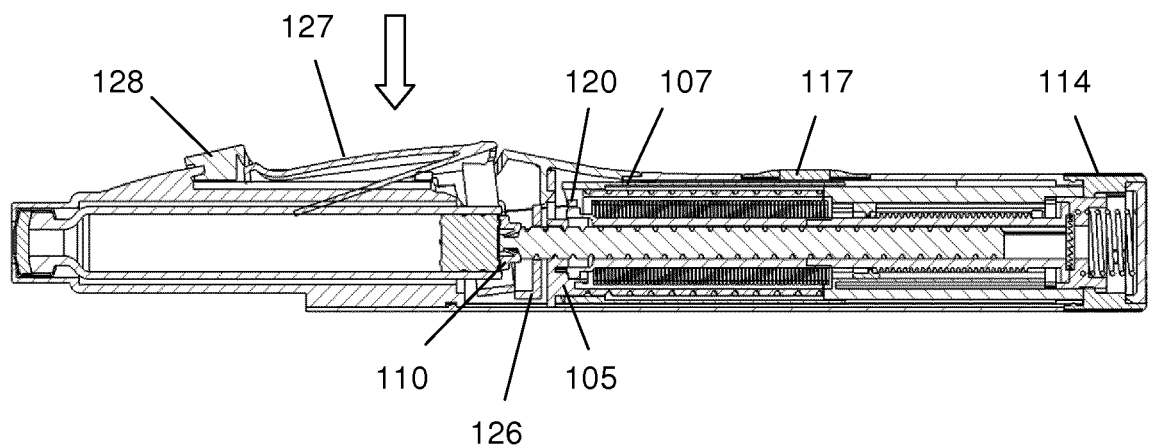
FIG. 6 shows a section view of the injection device of FIG. 5 during dose dispensing.
Figure 7:
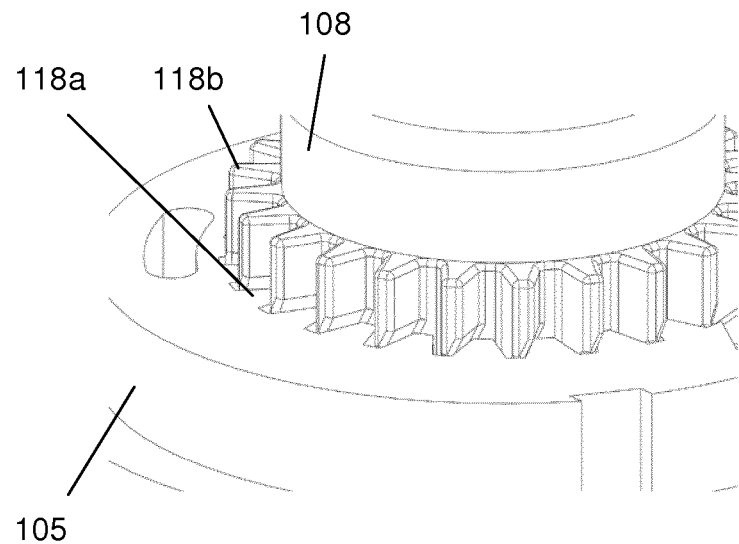
FIG. 7 shows a detail of the drive mechanism of FIG. 5 at the end of dose dispensing.
Figure 8:
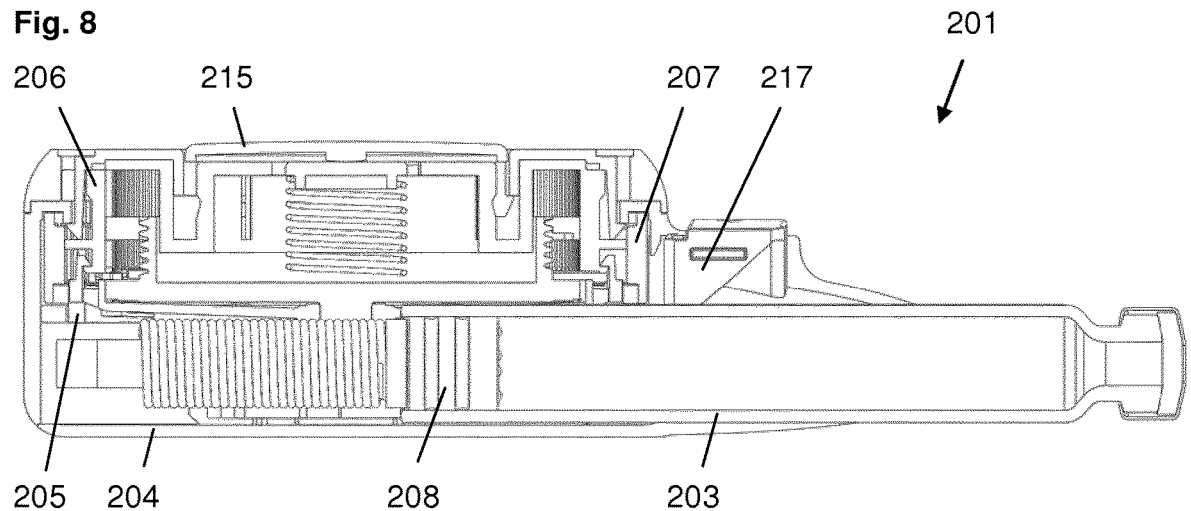
FIG. 8 shows a section view of an injection device comprising a drive mechanism according to a third embodiment of the invention during dose setting.
Figure 9:
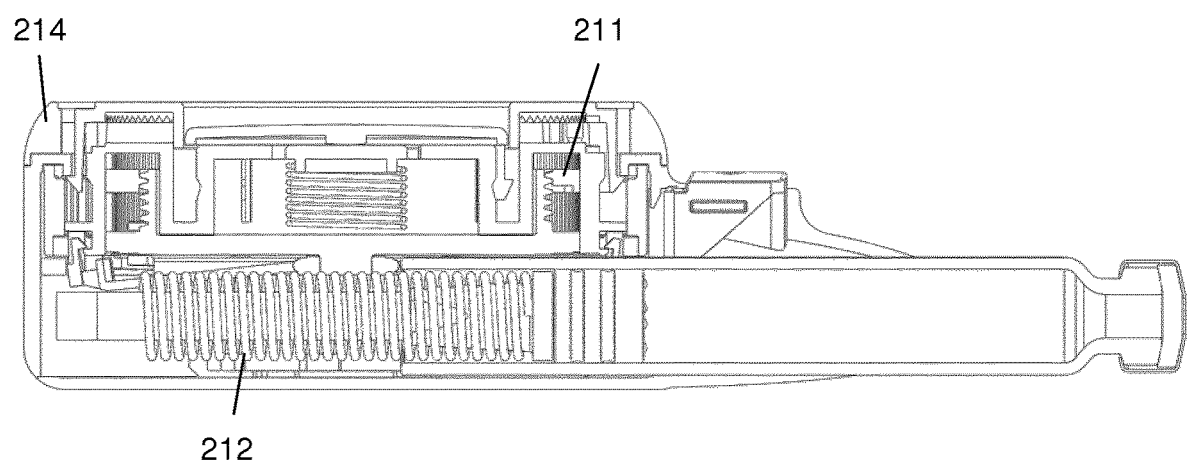
FIG. 9 shows a section view of the injection device of FIG. 8 during dose dispensing.

A second embodiment of a drive mechanism which is suitable for an injection device 101 is shown in FIGS. 5 to 7. The injection device 101 comprises a cartridge holder 102, a cartridge 103 containing a medicament, optionally a cap (not shown) and a drive mechanism. The drive mechanism comprises an outer housing 104 with a window 117, an inner housing 105, a dial member 106 (dial sleeve), a display member 107 (number sleeve), a drive member 108 (drive sleeve), a lead screw 109, a bearing 110, a nut 111, a torsion spring 112, a dial grip 114, a clutch plate 116, a first clutch 118, a second clutch 119, a ratchet feature 120, a clutch spring 125, a trigger clutch 126, a trigger 127 and a trigger cover 128.

Similar to the first embodiment, all components, except for the trigger 127 and the trigger cover 128, are located concentrically about a common principal axis of the drive mechanism.

The dial grip 114 is axially constrained to the outer housing 104. It is rotationally constrained, via a splined interface, to the dial member 106. As shown in FIG. 5, the dial member 106 is coupled to the drive member 108 via a ratchet interface (second clutch 119), which occurs on an axial abutment. The ratchet provides a detented position between the dial member 106 and the drive member 108 corresponding to each dose unit, and engages different ramped tooth angles during clockwise and anti-clockwise relative rotation. Corresponding ratchet teeth are provided on facing surfaces of the second clutch 119 (clutch plate) and the drive member 108. As an alternative, the clutch plate may be omitted providing the teeth directly on the dial member 106.

The display member 107 is rotationally constrained, via a splined interface, to the dial member 106. It is constrained to move along a helical path, relative to the inner housing 105, via a threaded interface. The display member 107 is marked with a sequence of numbers, which are visible through the window 117 in the outer housing 104, to denote the dialled dose of medicament.

The last dose nut 111 is located between the dial member 106 and the drive member 108. It is rotationally constrained to the dial member 106, via a splined interface. It moves along a helical path relative to the drive member 108, via a threaded interface, when relative rotation occurs between the dial member 106 and drive member 108. Again, the interfaces between the nut 111 and the dial member 106 and the drive member 108 may be opposite to the depicted embodiment.

The torsion spring 112 is attached at one end to the inner housing 105 and at the other end to the dial member 106. The attachments at both ends are configured to transfer tangential forces, resulting from torsion of the spring 112, and axial forces along the primary axis of the drive mechanism (longitudinal axis). The torsion spring 112 is pre-wound upon assembly, such that it applies a torque to the dial member 106 when the mechanism is at zero units dialled. The action of rotating the dial grip 114, to set a dose, rotates the dial grip 114 relative to the inner housing 105, and winds up the torsion spring 112. The torsion spring 112 may be designed in such a way as to exert an axial force which acts to pull the dial member 106 towards the inner housing 105. As an alternative, a separate compression spring may be provided biasing the drive member 108 in the distal direction as shown in FIGS. 5 and 6.

The lead screw 109 is rotationally constrained to the inner housing 105 via a splined interface. The lead screw 109 is forced to move axially relative to the inner housing 105, through its threaded interface to the drive member 108, when the drive member 108 moves relative to the inner housing 105. The bearing 110 (washer) is axially constrained to the lead screw 109 and acts on the bung within the liquid medicament cartridge 103.

The inner housing 105 is rigidly constrained to the outer housing 104. The axial abutment with the drive member 108 is provided by a pair of compliant arms which deflect during assembly. A pair of abutment features is provided at either end of the threaded interface with the display member 107, which limit the range of travel of the display member 107. These abutments provide the zero dose and maximum dose stops. The inner housing 105 provides a rotational constraint to the trigger clutch 126, and provides an axial abutment which reacts the axial force generated by the clutch spring 125. The axial position of the trigger clutch 126 is defined by the action of the clutch spring 125, which forces the trigger clutch 126 towards the cartridge end (distal end) of the drive mechanism, and its abutment with the trigger 127. When axially positioned in its at rest position, the trigger clutch 126 allows the drive member 108 to be in its distal position in which spline teeth 118a of the inner housing 105 engage with the spline teeth 118b on the drive member 108 which constrains the rotation of the drive member 108. The spline teeth 118a on the inner housing 105 and the corresponding spline teeth 118b on the drive member 108 form the first clutch 118. Engagement and disengagement of the first clutch 118 is shown in FIGS. 5 and 6. In other words, the drive member 108 is rotationally constrained to the inner housing 105, via engagement of a set of spline teeth 118a, 118b, when the trigger 127 is not activated. However, upon activation of the trigger 127, the trigger clutch 126 pushes the drive member 108 in the proximal direction which disengages first clutch 118. Teeth 118a, 118b are shown in FIG. 7 in more detail.

The clutch spring 125 is located between the inner housing 105 and the trigger clutch 126 and acts to force the trigger clutch 126 towards the cartridge end of the drive mechanism. The trigger 127 is constrained to pivot in the outer housing 104. It has an integral spring element, which acts to rotate the trigger 127 away from the outer housing 104. When the trigger 127 is depressed, an abutment is created with the trigger clutch 126, which moves the trigger clutch 126 axially towards the inner housing 105.

The outer housing 104 provides location for the liquid medication cartridge 103, the pivot for the trigger 127, an interface to rigidly constrain the inner housing 105, a window 117 through which the dose number on the display member 107 can be viewed, and a groove on its external surface to axially retain the dial grip 114. The trigger cover 128 may clip into the outer housing 104, and retains the trigger 127 within its pivot interface with the outer housing 104. The removable cap fits over the cartridge holder element 102 and is retained onto the outer housing 104 via clips when the drive mechanism is not in use. When the cap is fitted onto the outer housing 104, a mechanical interlock is created with the trigger 127, which prevents the trigger from being depressed from its at rest position.

With the device in the at rest condition, the display member 107 is positioned against its zero dose abutment with the inner housing 105 and the trigger 127 is not depressed. Dose marking '0' on the display member 107 is visible through the window 117 on the outer housing 104. As shown in FIG. 5, the trigger clutch 126 is in a distal position, which is the position for dose setting and dose resetting.

As the user rotates the dial grip 114, the dial member 106 rotates relative to the drive member 108. Rotation of the dial member 106 generates rotation in the display member 107, which travels along its helical path defined by its interface with the inner housing 105. The device is now set to deliver liquid medicament. The user may now choose to increase the selected dose by continuing to rotate the dial grip 114 in the clockwise direction. With the drive mechanism in a state in which a dose has been selected, the user is able to deselect any number of units from this dose. Deselecting a dose is achieved by the user rotating the dial grip 114 anti-clockwise, which returns the display member 107 towards the zero dose position.

With the mechanism in a state in which a dose has been selected, the user is able to activate the drive mechanism to commence delivery of a dose. Delivery of a dose is initiated by the user depressing the trigger 127 on the side of the drive mechanism. As the trigger is depressed, an abutment is created with the trigger clutch 126 which acts to move the trigger clutch axially away from the cartridge 103, i.e. in the proximal direction, against the action of the clutch spring 125. When the trigger 127 is fully depressed, sufficient axial travel has occurred in the trigger clutch 126 to disengage spline teeth 118a, 118b of the first clutch.

After dose dispensing, the trigger 127 is released allowing the drive member 108 teeth 118b to re-engage with the teeth 118a of the inner body 105. The position of these teeth 118a, 118b relative to the zero dose stop position of number sleeve 107 is such that the drive member 108 rotates fractionally when the teeth 118a, 118b engage, backwinding the lead screw 109 away from the cartridge bung. This helps to eliminate weeping during subsequent setting operations. This rotation of the drive member 108 is caused by an angled or ramped design of the teeth 118a, 118b as mentioned above with respect to the first embodiment.

A third embodiment is depicted in FIGS. 8 to 12. The injection device 201 comprises a cartridge 203, a housing 204 and a chassis 205 (inner housing body). A dial gear 206 (dial member) is splined to a number wheel 207 and translated axially by a button 215. Further, the dial gear 206 is splined to a release gear 208 (drive member) during dose dispensing. The number wheel 207 is a display member which displays numbers. A prism 217 is provided which magnifies and reflects the numbers displayed on the number wheel 207. A last dose nut 211 is splined to the dial gear 206 and threaded to the release gear 208. A belt is retained in a belt drum and a ferrule and passes over a roller in the chassis 205. A compression spring 212 is provided as a pre-stressed drive spring acting on a piston rod 209. The spring 212 is fitted between chassis 205 and the ferrule. The release gear 208 is geared to the belt drum and retained in the chassis 205 during dose setting, whereas it is splined to the dial gear 206 during dose dispensing.

A dial 214 which is rotationally coupled to the dial gear via face teeth is rotated clockwise to set a dose. Detents between the dial 214 and a front casework provide discrete dose set positions. The release gear 208 is rotationally fixed by the chassis 205. The number wheel 207 is driven directly from the dial gear 206 with zero dose and maximum dose stops provided between the number wheel and the chassis. The last dose nut 211 is rotated by the dial gear 206 up the thread on the release gear towards a last dose stop. In the similar way, a set dose may be decreased by rotating the dial anti-clockwise.

To dispense a dose, the button 215 is depressed, locking the dial 214. The dial gear 206 engages with the release gear 208 and pushes locking arms of the chassis out of engagement from the release gear 208, allowing this to rotate under the action of the spring 212. Rotation of the release gear 208 allows the belt drum to rotate, releasing the belt and allowing the spring 212 to act on and advance the cartridge bung.

Figure 11:
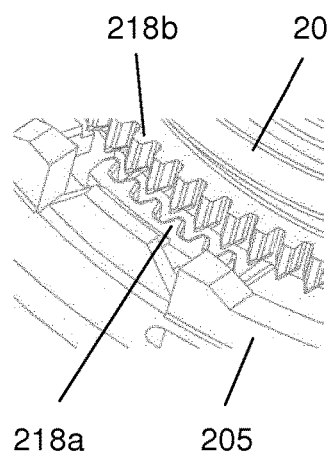
FIG. 11 shows an enlarged detail of the drive mechanism of FIG. 8 prior to engagement of the first clutch.
Figure 12:
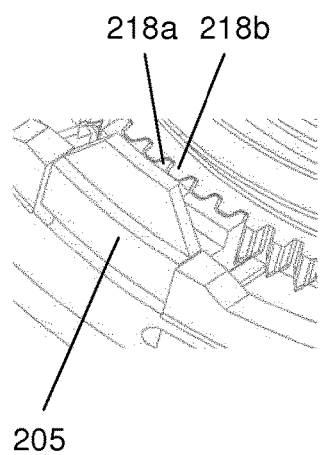
FIG. 12 shows an enlarged detail of the drive mechanism of FIG. 8 after engagement of the first clutch.
Figure 10:
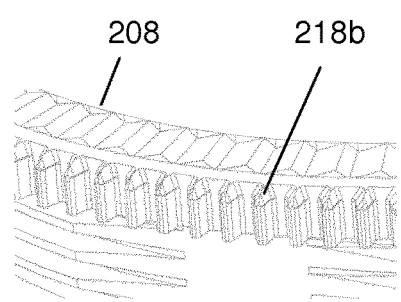
FIG. 10 shows a detail of the drive mechanism of FIG. 8.

FIGS. 10 to 12 show in more detail that the release gear 208 is provided on its radially outer surface with splines 218b that engage with corresponding splines 218a of the chassis 205, preferably on locking arms of the chassis. Teeth 218a, 218b form a first clutch 218. FIG. 10 shows that the splined teeth 218b are angled such that the release gear 208 is turned against the torque induced by the spring 212 as they re-engage when the button 215 is released. This back-winding of the release gear 208 ensures that the chassis locking arms react the spring force in place of the zero unit stop as the button 215 is released. This prevents the release gear 208 rotating to take up clearance at this interface when the subsequent dose is dialled (and the zero unit stop is disengaged), which could lead to the dispense of some fluid.

FIG. 10 shows ramp features on teeth 218b which create a back-winding of the release gear as it engages with the teeth of the chassis 205. However, in addition to said ramp features or as an alternative to the ramp features a whole surface of the splines may be angled to generate back-winding.

A fourth embodiment is depicted in FIGS. 13 to 16. Main components of the injection device 301 are a cartridge 303, an outer housing 304, an inner housing body 305 (spool), a drive sleeve 308 (drive member), a dial sleeve 306 (dial member), a piston rod in the form of a lead screw 309, a dose nut 307, a last dose nut 311, a dose dial grip 314 forming a button or trigger 315 and a spring 312, which is a flat spring or tensioning element.

The spring 312 is provided on two spools between the inner body 305 and the drive sleeve 308. The drive sleeve 308 is rotationally fixed by the outer housing 304 during dose setting and dose resetting. The lead screw 309 is splined to the drive sleeve 308 and threaded to the inner body 305. The dial sleeve 306 is coupled to the drive sleeve 308 via a detent and clutched connection. The dose dial grip 314 is splined to the dial sleeve 306 during dose setting and dose resetting. A last dose nut 311 is splined to the dial sleeve 306 and threaded to the drive sleeve 308.

Figure 13:
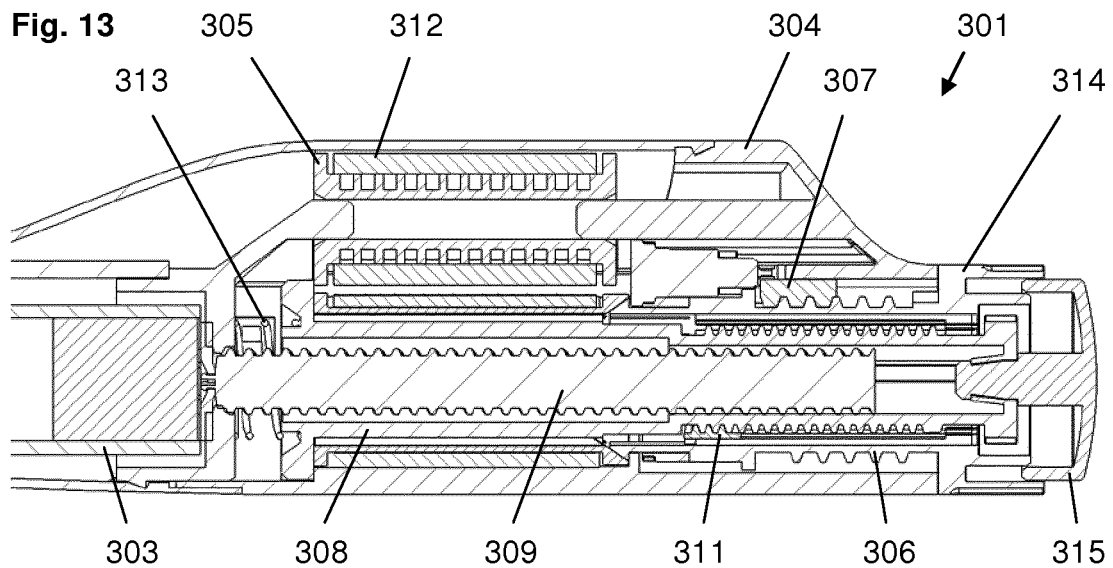
FIG. 13 shows a section view of an injection device comprising a drive mechanism according to a fourth embodiment of the invention during dose setting.

For dose setting the dose dial grip 314 is rotated clockwise by the user. This causes the dial sleeve 306 to rotate, moving a number sleeve 307 away from its zero dose stop feature and increasing the dose displayed. In the example of FIG. 13, the dose counter consists of the dial sleeve 306 with printed units and a tens wheel which is incremented by the action of an index gear once per revolution. The last dose nut 311 rotates on a thread on the drive sleeve 308 towards the last dose stop. During dose setting the drive sleeve 308 is coupled to the outer housing 304 via splines 318a, 318b of a first clutch 318 provided at the distal ends of the drive sleeve 308 and the housing 304. Teeth 318a, 318b are biased into engagement by a trigger spring 313. Thus, the drive sleeve 308 is locked by its splined engagement with the housing 304, thus preventing it from being rotated by the spring 312 which in turn prevents rotation of the output spool (drive sleeve spool) and the lead screw 309.

To dispense a dose, the dose dial grip 314 is depressed. This disengages the dose dial grip 314 from the dial sleeve 306 so that it does not rotate during dispense. The drive sleeve 308 is moved axially with the dose dial grip 314, disengaging the splined engagement with the outer housing 304 allowing the spring 312 to rotate drive sleeve 308. The drive sleeve 308 winds the lead screw 309 forwards through the thread in the inner body 305 to advance the cartridge bung. The odometer counter mechanism and the dose nut 307 then return towards their zero dose positions.

Figure 14:
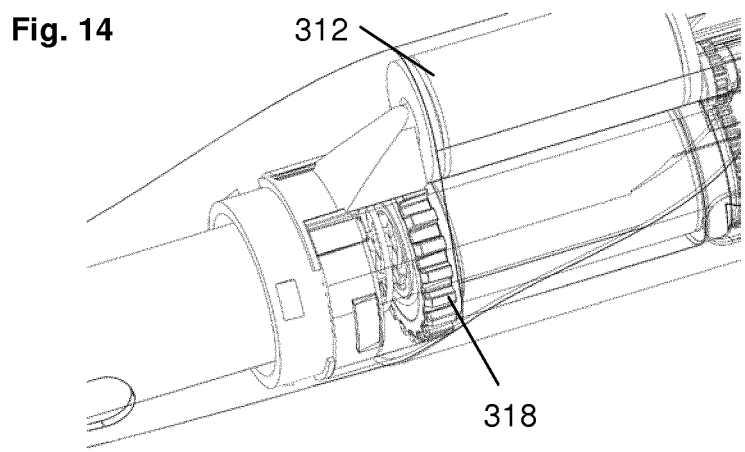
FIG. 14 shows a detail of the drive mechanism of FIG. 13.
Figure 15:
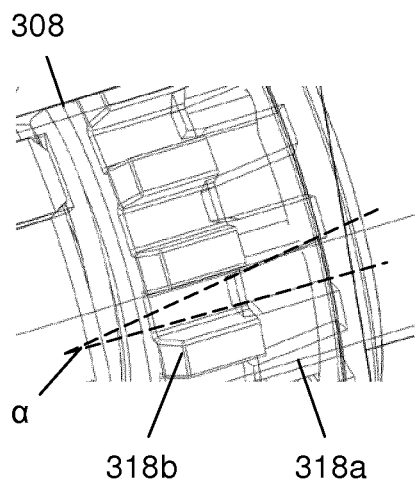
FIG. 15 shows an enlarged detail of the drive mechanism of FIG. 13 at the start of engagement of the first clutch.
Figure 16:
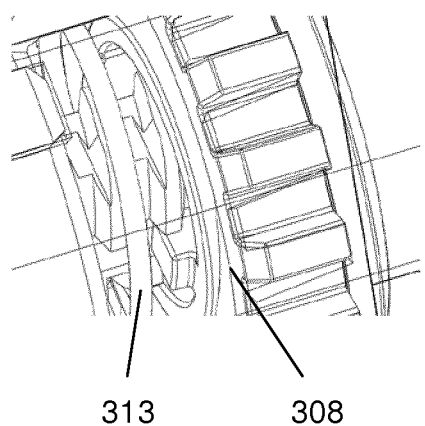
FIG. 16 shows an enlarged detail of the drive mechanism of FIG. 13 at the end of engagement of the first clutch.

As can be seen in FIGS. 14 to 16, the spline teeth 318a in the outer housing 304 that engage with the teeth 318b of the drive sleeve 308 are inclined by an angle a with respect to an orientation in the longitudinal direction of the drive mechanism. Thus, the drive sleeve 308 is turned against the spring torque as teeth 318a, 318b re-engage when the trigger 315 is released. Back-winding the drive sleeve 308 retracts the lead screw assembly 309 and ensures that the drive sleeve to body splines 318a, 318b act as the end of dose stop in place of the dose nut 307. The back-winding of the drive sleeve 308 removes the effect of clearances within the mechanism (as a result of designing for manufacturing tolerances or assembly) which could otherwise lead to slight advancement of the lead screw 309 and medicament dispense when the device is dialled for the subsequent dose.

A fifth embodiment (not shown) may be similar regarding the main function and components as described above with respect to the fourth embodiment. However, in contrast to the fourth embodiment which has the lead screw 309 arranged coaxially with the dial sleeve 306 and the drive sleeve 308, in the fifth embodiment the lead screw may be arranged spaced from and parallel to the drive sleeve 308 and the dial sleeve 306. A drive tube, which is geared to the drive sleeve 308 may be provided as a driven member which is splined to the lead screw 309.

The invention claimed is:

1. A drive mechanism, for an injection device, having a distal end and an opposite proximal end, the drive mechanism comprising:
   a housing;
   a piston rod at least axially movable relative to the housing; and
   a drive member coupled to the housing via a first clutch such that a relative rotation of the drive member about an axis of rotation with respect to the housing is inhibited during dose setting and is allowed during dose dispensing, the drive member engaging the piston rod such that a rotation of the drive member causes an axial movement of the piston rod,
   wherein engagement of the first clutch causes rotation of the drive member with respect to the housing in a direction to move the piston rod in a proximal direction.

2. The drive mechanism according to claim 1, wherein the engagement of the first clutch is effected by a relative axial movement of the drive member with respect to the housing.

3. The drive mechanism according to claim 1, wherein the first clutch comprises first teeth on the drive member and corresponding second teeth on the housing, and the first clutch is configured to be engaged when the first teeth are engaged with the second teeth such that rotation of the drive member with respect to the housing in the direction moves the piston rod in the proximal direction.

4. The drive mechanism according to claim 3, wherein at least one of the first teeth or the second teeth comprise a surface inclined by an angle of 1 degree to 50 degrees to a plane parallel to the axis of rotation of the drive member.

5. The drive mechanism according to claim 3, wherein the housing comprises an inner body rotationally constrained to an outer housing, wherein the second teeth are provided on the inner body.

6. The drive mechanism according to claim 5, comprising a number sleeve in threaded engagement with the housing or the inner body and movable between a zero dose position and a maximum dose position,
   wherein a zero dose stop inhibits relative movement of the number sleeve with respect to the housing or the inner body in one rotational direction.

7. The drive mechanism according to claim 6, wherein a position of the first and second teeth relative to a position of the zero dose stop is such that the first clutch causes the drive member to rotate when the first and second teeth engage in the zero dose position of the number sleeve.

8. The drive mechanism according to claim 1, further comprising:

a dose setting member,
a torsion spring arranged between the housing and the dose setting member,
a second clutch rotationally de-coupling the drive member and the dose setting member during the dose setting and coupling the drive member to the dose setting member during the dose dispensing, and
a button provided on the proximal end of the drive mechanism, wherein actuation of the button causes axial displacement of the drive member, de-coupling of the first clutch, and coupling of the second clutch.

9. The drive mechanism according to claim 1, further comprising:
a dose setting member,
a torsion spring arranged between the housing and the dose setting member,
a second clutch rotationally de-coupling the drive member and the dose setting member during the dose setting and coupling the drive member to the dose setting member during the dose dispensing, and
a trigger provided on a side of the housing, wherein actuation of the trigger causes axial displacement of a trigger clutch acting on the drive member, de-coupling of the first clutch, and coupling of the second clutch.

10. The drive mechanism according to claim 1, further comprising:
a dose setting member,
a compression spring arranged between the housing and the piston rod,
a second clutch rotationally de-coupling the drive member and the dose setting member during the dose setting and coupling the drive member to the dose setting member during the dose dispensing, and
a button, wherein actuation of the button causes axial displacement of the dose setting member, de-coupling of the first clutch and coupling of the second clutch.

11. The drive mechanism according to claim 1, further comprising:
a dose setting member,
a flat spring arranged between the housing and the drive member,
a second clutch rotationally de-coupling the drive member and the dose setting member during the dose setting and coupling the drive member to the dose setting member during the dose dispensing, and
a button provided on the proximal end of the drive mechanism, wherein actuation of the button causes axial displacement of the drive member, de-coupling of the first clutch, and coupling of the second clutch.

12. The drive mechanism according to claim 1, wherein the first clutch includes a first state in which the first clutch couples the drive member to the housing and a second state in which the drive member is decoupled from the housing.

13. An injection device comprising:
a housing;
a cartridge containing a medicament; and
a drive mechanism having a distal end and a proximal end, the drive mechanism comprising
a piston rod at least axially movable relative to the housing, and
a drive member coupled to the housing via a first clutch such that a relative rotation of the drive member about an axis of rotation with respect to the housing is inhibited during dose setting and is allowed during dose dispensing, the drive member engaging the piston rod such that a rotation of the drive member causes an axial movement of the piston rod,
wherein engagement of the first clutch causes rotation of the drive member with respect to the housing in a direction to move the piston rod in a proximal direction.

14. The injection device according to claim 13, wherein the drive mechanism further comprises:
a dose setting member,
a compression spring arranged between the housing and the piston rod,
a second clutch rotationally de-coupling the drive member and the dose setting member during the dose setting and coupling the drive member to the dose setting member during the dose dispensing, and
a button, wherein actuation of the button causes axial displacement of the dose setting member, de-coupling of the first clutch and coupling of the second clutch,
wherein the compression spring is pre-tensioned to store energy required to dispense the whole contents of the cartridge.

15. The injection device according to claim 13, wherein the drive mechanism further comprises:
a dose setting member,
a flat spring arranged between the housing and the drive member,
a second clutch rotationally de-coupling the drive member and the dose setting member during the dose setting and coupling the drive member to the dose setting member during the dose dispensing, and
a button provided on the proximal end of the drive mechanism, wherein actuation of the button causes axial displacement of the drive member, de-coupling of the first clutch, and coupling of the second clutch,
wherein the flat spring is pre-tensioned to store energy required to dispense the whole contents of the cartridge.

* * * * *